(12) United States Patent
Shrawat et al.

(10) Patent No.: US 9,593,083 B2
(45) Date of Patent: Mar. 14, 2017

(54) CRYSTALLINE ERLOTINIB HYDROCHLORIDE PROCESS

(71) Applicant: Shilpa Medicare Limited, Raichur (IN)

(72) Inventors: Vimal Kumar Shrawat, Raichur (IN); Prashant Purohit, Raichur (IN); Rafiuddin Dr., Raichur (IN); Vinod Kumar Singh, Raichur (IN); Akshay Kant Chaturvedi, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 0 days.

(21) Appl. No.: 14/418,449

(22) PCT Filed: Aug. 14, 2013

(86) PCT No.: PCT/IN2013/000500
§ 371 (c)(1),
(2) Date: Jan. 30, 2015

(87) PCT Pub. No.: WO2014/037961
PCT Pub. Date: Mar. 13, 2014

(65) Prior Publication Data
US 2015/0299141 A1    Oct. 22, 2015

(30) Foreign Application Priority Data

Sep. 4, 2012  (IN) .......................... 3637/CHE/2012

(51) Int. Cl.
*C07D 239/94*    (2006.01)

(52) U.S. Cl.
CPC ........ *C07D 239/94* (2013.01); *C07B 2200/13* (2013.01)

(58) Field of Classification Search
CPC .................................................. C07D 239/94
See application file for complete search history.

(56) References Cited

U.S. PATENT DOCUMENTS

| | | | |
|---|---|---|---|
| 5,747,498 A | 5/1998 | Schnur et al. | |
| 6,476,040 B1 | 11/2002 | Norris et al. | |
| 6,900,221 B1 | 5/2005 | Norris et al. | |
| 7,148,231 B2 | 12/2006 | Bubendorf et al. | |
| 8,372,856 B2 * | 2/2013 | Westheim ............ | C07D 239/94 514/266.3 |
| 2005/0130995 A1 | 6/2005 | Nishino et al. | |
| 2006/0154941 A1 | 7/2006 | Huang | |
| 2008/0058355 A1 | 3/2008 | Westheim | |
| 2008/0167327 A1 | 7/2008 | Westheim | |
| 2010/0004449 A1 * | 1/2010 | Gavenda ............... | C07D 239/94 544/293 |
| 2010/0261738 A1 | 10/2010 | Jyothi Prasad et al. | |
| 2012/0101272 A1 | 4/2012 | Murugesan et al. | |
| 2014/0121373 A1 * | 5/2014 | Singh ................... | C07D 239/94 544/293 |

FOREIGN PATENT DOCUMENTS

| | | |
|---|---|---|
| EP | 0817775 B1 | 9/2001 |
| EP | 1044969 B1 | 12/2006 |
| WO | 99/55683 A1 | 11/1999 |
| WO | 01/34574 A1 | 5/2001 |
| WO | 2004072049 A1 | 8/2004 |
| WO | 2007060691 A2 | 5/2007 |
| WO | 2007138612 A2 | 12/2007 |
| WO | 2008000418 A2 | 1/2008 |
| WO | 2008012105 A1 | 1/2008 |
| WO | 2008049645 A2 | 5/2008 |
| WO | 2008102369 A1 | 8/2008 |
| WO | 2008122776 A2 | 10/2008 |
| WO | 2009002538 A2 | 12/2008 |
| WO | 2009007984 A2 | 1/2009 |
| WO | 2009024989 A2 | 2/2009 |
| WO | 2009025873 A2 | 2/2009 |
| WO | 2009025876 A2 | 2/2009 |

* cited by examiner

*Primary Examiner* — Sun Jae Yoo

(57) ABSTRACT

The present invention provides process for preparation of Crystalline Erlotinib HCl (I) Form-SE

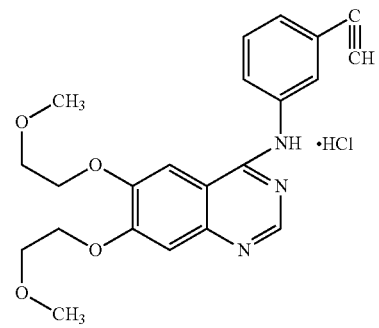

(I)

characterized by X-ray powder diffraction pattern comprising at least 5 characteristic 2θ° peaks selected from the XRPD peak set of 5.60, 10.00, 11.40, 13.00, 13.50, 15.20, 18.40, 20.65, 21.86, 23.5, 31.80, 32.13, 32.80, 34.40±0.20 2θ°, DSC isotherm comprising the endothermic peaks ranging between 213 to 217° C. (Peak −1) and 225 to 235° C. (Peak −2) and IR absorption characteristic peaks at approximately 3278 $cm^{-1}$, 1948 $cm^{-1}$, 1871 $cm^{-1}$, 1632 $cm^{-1}$, 1164 $cm^{-1}$, 1024 $cm^{-1}$, 940 $cm^{-1}$ and 742 $cm^{-1}$ useful as active pharmaceutical ingredient in pharmaceutical compositions for the treatment cancer.

1 Claim, 4 Drawing Sheets

CRYSTALLINE ERLOTINIB HYDROCHLORIDE PROCESS

INTRODUCTION

Erlotinib hydrochloride (I) is chemically known as N-(3-ethynylphenyl)-6,7-bis(2-methoxy ethoxy)-4-quinazolinamine hydrochloride

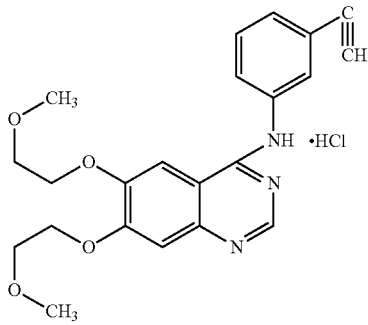

(I)

It is indicated for the treatment of patients with locally advanced or metastatic non-small cell lung cancer after failure of at least one prior chemotherapy regimen, and in combination with gemcitabine is indicated for the first-line treatment of patients with locally advanced, unresectable or metastatic pancreatic cancer.

Schnur, et al in U.S. Pat. No. 5,747,498 and EP0817775B1 disclose a process for the preparation of Erlotinib free base and its HCl salt, which follows the pathway as given in the Scheme-1.

N-(3-ethynylphenyl)-6,7-bis(2-methoxyethoxy)-4-quinazolinamine (Erlotinib) base is separated chromatographically and converted to the hydrochloride salt in a solvent, such as, chloroform using hydrochloric acid. Though the disclosure provide some acid-addition salt e.g. hydrochloric, hydrobromic, sulphuric, phosphoric, methanesulfonic, benzenesulfonic, trifluoroacetic, citric, lactic or maleic acid, however, it only demonstrates predominately the process for the preparation of erlotinib hydrochloride.

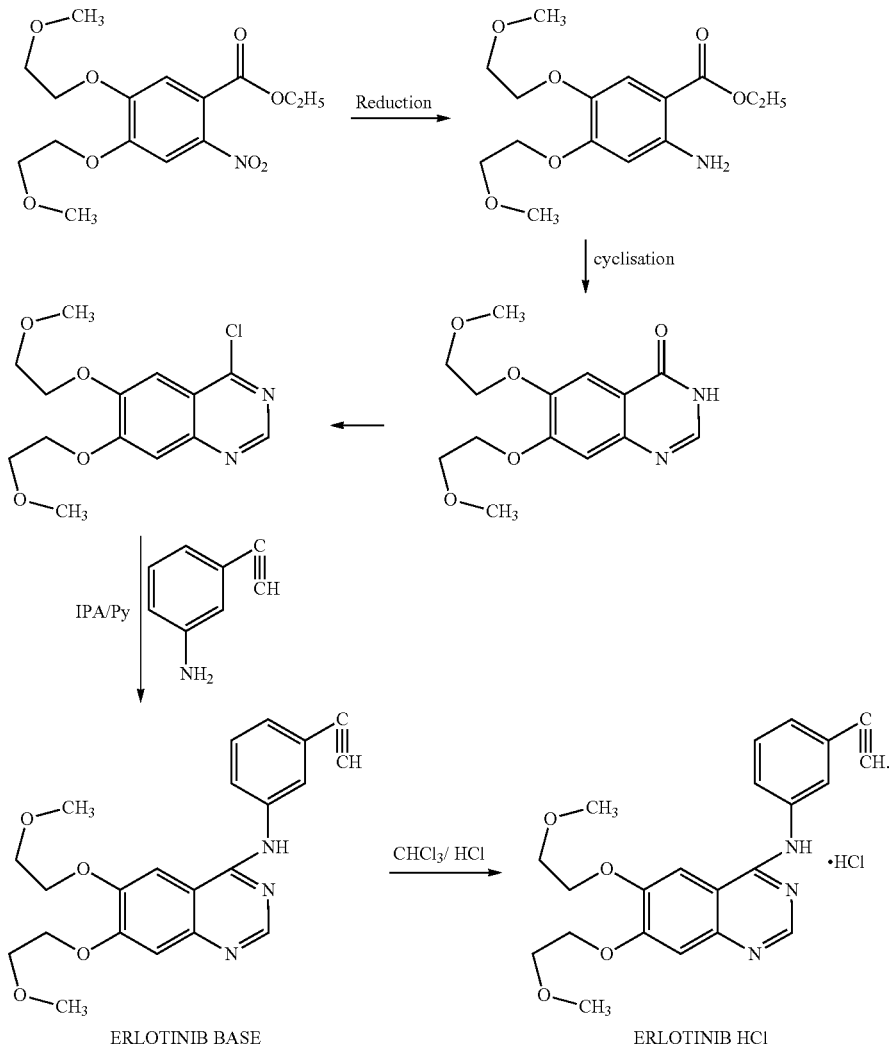

Scheme-1: Process as disclosed in U.S. Pat. No. 5,747,498

EP1044969B1 provides a process for preparing N-(3-ethynylphenyl)-6,7-bis(2-methoxyethoxy)quinazolin-4-amine which involves stirring 4-[3-[[6,7-bis(2-methoxyethoxy)-4-quinazolinyl]amino]phenyl]-2-methyl-3-butyn-2-ol with anhydrous sodium hydroxide and 2-methoxyethanol and heating at reflux for 47 hours. The reaction mixture is cooled to 20 to 25 degree C. and concentrated hydrochloric acid is added to it. The resulting mixture is granulated at 20 to 25° C. to crystallize the product.

WO 2007/138612 provides a process for preparation of N-(3-ethynylphenyl)-6,7-bis(2-methoxyethoxy)-4-quinazolinamine hydrochloride which involves treatment in the end with a polar solvent containing hydrochloric acid with Erlotinib free base to provide Erlotinib hydrochloride.

Norris et al in WO 01/34574 and its equivalent U.S. Pat. No. 6,900,221 described polymorphic Forms-A and B of Erlotinib HCl, and mentioned that the polymorphic form 'B' is thermodynamically more stable. This patent, also described that product obtained as per U.S. Pat. No. 5,747,498 was a mixture of polymorphic Forms A and B.

Further, Norris et al in U.S. Pat. No. 6,900,221 also disclosed a method of preparing pure polymorphic Form-B of Erlotinib HCl (I) that exhibits an X-ray powder diffraction pattern having characteristic peaks expressed in degrees 2-theta at approximately 6.26, 12.48, 13.39, 16.96, 20.20, 21.10, 22.98, 24.46, 25.14 and, 26.91, which is free of the A polymorph.

Bubendorf et al in U.S. Pat. No. 7,148,231 and its corresponding International Application published as WO 2004/072049 disclosed a novel polymorph E along with its DSC and XRD characteristics. This crystalline polymorphic form E is prepared particularly in (α,α,α)-trifluoro toluene, which is highly flammable and dangerous for the environment. The solvent is not only expensive solvent but also have inconvenience to handle on industrial scale.

Jyothi Prasad Ramanadham et al in US 20100261738 A1 disclosed other stable polymorphic forms of Erlotinib HCl designated as Form-M, Form-N and Form-P. These forms were prepared from solvent systems selected from methanol with a solution of HCl in dry methanol or isopropanol (Form-M); isopropanol with isopropanolic HCl (Form-N) and methylene chloride with isopropanolic HCl (Form-P).

Murugesan Balaguru et al in US 20120101272 A1 disclosed Erlotinib trifluoroacetate salt as Form E characterized by a powder XRD pattern comprising peak 2θ values at about 6.43±0.2θ, 16.73±0.2θ, 22.55±0.2θ, 25.72±0.2θ, and 26.25±0.2θ.

Besides the above disclosures various other disclosures includes U.S. Pat. No. 6,476,040; US2005/0130995; US2006/0154941; US2008/0167327 A1; US2008/0058355 A1; WO 99/55683; WO2003/066602 A1; WO2007/060691; WO 2008/000418 A2; WO2008/012105; WO2008/049645; WO2008/102369; WO 2008/122776; WO2009/002538; WO2009/007984; WO2009/024989; WO 2009/025873 A2; WO2009/025876 A2 dealt with either process or intermediates for Erlotinib.

Being erlotinib hydrochloride as an important anticancer therapeutic agent, additional and improved ways of preparing erlotinib hydrochloride salt may be of immense value to pharmaceutical science and the healthcare of cancer patients. Hence, there exists a need in the development of new stable crystalline form and economically viable processes, which may be commercially up scalable, viable, safer for handling, less time consuming and with better and consistent quality parameters.

The present inventors have found a new Crystalline form of Erlotinib HCl (I) designated as Form-SE, which is stable and free from any contamination of Form-A and B along with a process for preparation thereof.

SUMMARY OF INVENTION

Particular aspects of the present application relates to the process/es for preparation of Erlotinib hydrochloride (I).

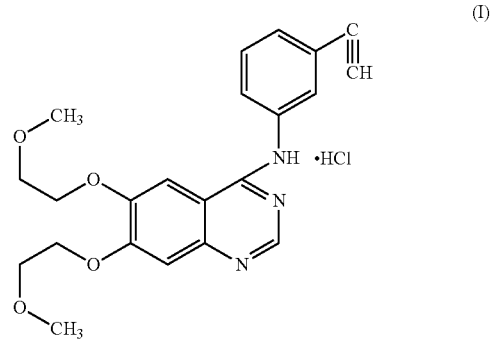 [SMILES: C#Cc1cccc(Nc2ncnc3cc(OCCOC)c(OCCOC)cc23)c1 ; Cl]

The application relates to process for preparation of Erlotinib HCl (I) and its stable crystalline polymorphic form designated as Form-SE, which is substantially free from process related impurities as well as contamination of Form A and Form B. The crystalline polymorphic forms of Erlotinib HCl (I) obtained by the processes according to the present invention are useful as active pharmaceutical ingredient in pharmaceutical compositions for treating hyperproliferative disorders, such as cancer, by administering the compound in a composition. Different aspects of the present application are summarized herein below individually.

In one aspect of the present application, it relates to Erlotinib hydrochloride (I) crystalline

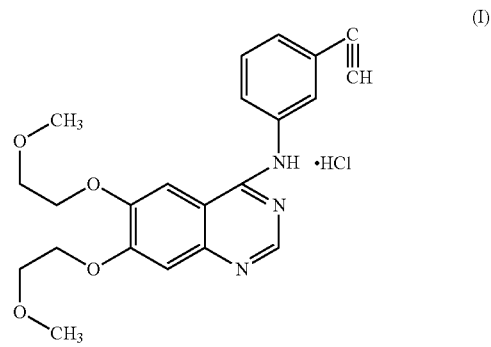 [SMILES: C#Cc1cccc(Nc2ncnc3cc(OCCOC)c(OCCOC)cc23)c1 ; Cl]

Form-SE characterized by X-ray powder diffraction pattern comprising at least 5 characteristic 2θ° peaks selected from the XRPD peak set of 5.60, 10.00, 11.40, 13.00, 13.50, 15.20, 18.40, 20.65, 21.86, 23.5, 31.80, 32.13, 32.80, 34.40±0.20 2θ°.

Erlotinib hydrochloride crystalline Form-SE is further characterized by DSC isotherm comprising at least two endothermic peaks ranging between—
a. Peak −1—Between 213 to 217° C.
b. Peak −2—Between 225 to 235° C.

In a further aspect, it relates to Erlotinib hydrochloride crystalline Form-SE, which has an IR absorption spectrum having characteristic peaks expressed in cm$^{-1}$ approximately 3278 cm$^{-1}$, 1948 cm$^{-1}$, 1871 cm$^{-1}$, 1632 cm$^{-1}$, 1164 cm$^{-1}$, 1024 cm$^{-1}$, 940 cm$^{-1}$ and 742 cm$^{-1}$.

Erlotinib hydrochloride crystalline Form-SE of the present invention it relates to characterization by X-ray powder diffraction pattern substantially according to FIG. 1, DSC isothermal pattern substantially according to FIG. 2 and IR absorption spectrum substantially according to FIG. 3.

In yet another aspect of the present invention, it relates a process for preparing Erlotinib hydrochloride crystalline Form-SE characterized by X-ray powder diffraction pattern comprising at least 5 characteristic 2θ° peaks selected from the XRPD peak set of 5.60, 10.00, 11.40, 13.00, 13.50, 15.20, 18.40, 20.65, 21.86, 23.5, 31.80, 32.13, 32.80, 34.40±0.20 2θ°, DSC isotherm comprising the endothermic peaks ranging between 213 to 217° C. (Peak -1) and 225 to 235° C. (Peak -2) and IR absorption characteristic peaks at approximately 3278 cm$^{-1}$, 1948 cm$^{-1}$, 1871 cm$^{-1}$, 1632 cm$^{-1}$, 1164 cm$^{-1}$, 1024 cm$^{-1}$, 940 cm$^{-1}$ and 742 cm$^{-1}$ comprising the steps of— a. Combining the Erlotinib free base or salt with a mixture of ketone and alcohol solvent both having water content upto less than 0.5% w/w
b. raise the temperature upto about 40-70° C.
c. Stir the solution at same temperature up to a time between 15 to 60 minutes.
d. combine isopropanol and HCl mixture
e. optionally maintain the mixture for 10-60 minutes
f. cooling the mixture upto about 10-40° C.
g. isolating the crystalline material In yet another aspect, the Crystalline Form SE of Erlotinib HCl obtained by the process/es of the present application may be formulated as solid compositions for oral administration in the form of capsules, tablets, pills, powders or granules useful in the treatment of hyper-proliferative disorders, such as cancer.

Further aspects of the present invention are demonstrated in detailed description section as well as examples.

DETAILED DESCRIPTION

As set forth herein, aspects of the present invention provides crystalline polymorphic form SE of Erlotinib HCl (I) and processes for preparation thereof.

Individual embodiments of the present invention are detailed herein below separately.

In one embodiment of the present application, it provides Erlotinib hydrochloride (I) crystalline

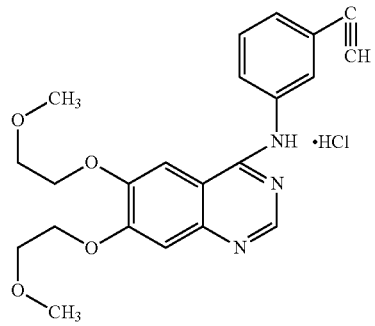 [SMILES: C#Cc1cccc(Nc2ncnc3cc(OCCOC)c(OCCOC)cc23)c1 ; Cl]

Form-SE characterized by X-ray powder diffraction pattern comprising at least 5 characteristic peaks at diffraction angles (expressed in 2θ°) selected from the XRPD peak set of 5.60, 10.00, 11.40, 13.00, 13.50, 15.20, 18.40, 20.65, 21.86, 23.5, 31.80, 32.13, 32.80, 34.40±0.20 2θ°.

Erlotinib hydrochloride crystalline Form-SE is further characterized by DSC isotherm comprising at least two endothermic peaks ranging between—
a. Peak -1—Between 213 to 217° C.
b. Peak -2—Between 225 to 235° C.

The characteristic peaks and their d spacing values of the new crystalline Form-SE are tabulated in the Table-1.

TABLE 1

Characteristic XRPD Peaks of Crystalline Form-SE

| S. No. | Angle (2θ°) ± 0.20 | d Spacing Value (A°) |
|---|---|---|
| 1. | 5.64 | 15.66 |
| 2. | 10.05 | 8.79 |
| 3. | 11.32 | 7.80 |
| 4. | 13.00 | 6.80 |
| 5. | 13.54 | 6.53 |
| 6. | 15.19 | 5.82 |
| 7. | 18.47 | 4.80 |
| 8. | 20.65 | 4.29 |
| 9. | 21.86 | 4.06 |
| 10. | 23.53 | 3.77 |
| 11. | 31.79 | 2.81 |
| 12. | 32.13 | 2.78 |
| 13. | 32.78 | 2.72 |
| 14. | 34.46 | 2.60 |

In another embodiment, Erlotinib hydrochloride crystalline Form-SE, which has an IR absorption spectrum having characteristic peaks expressed in cm$^{-1}$ at approximately 3278 cm$^{-1}$, 1948 cm$^{-1}$, 1871 cm$^{-1}$, 1632 cm$^{-1}$, 1164 cm$^{-1}$, 1024 cm$^{-1}$, 940 cm$^{-1}$ and 742 cm$^{-1}$.

Figure 1:
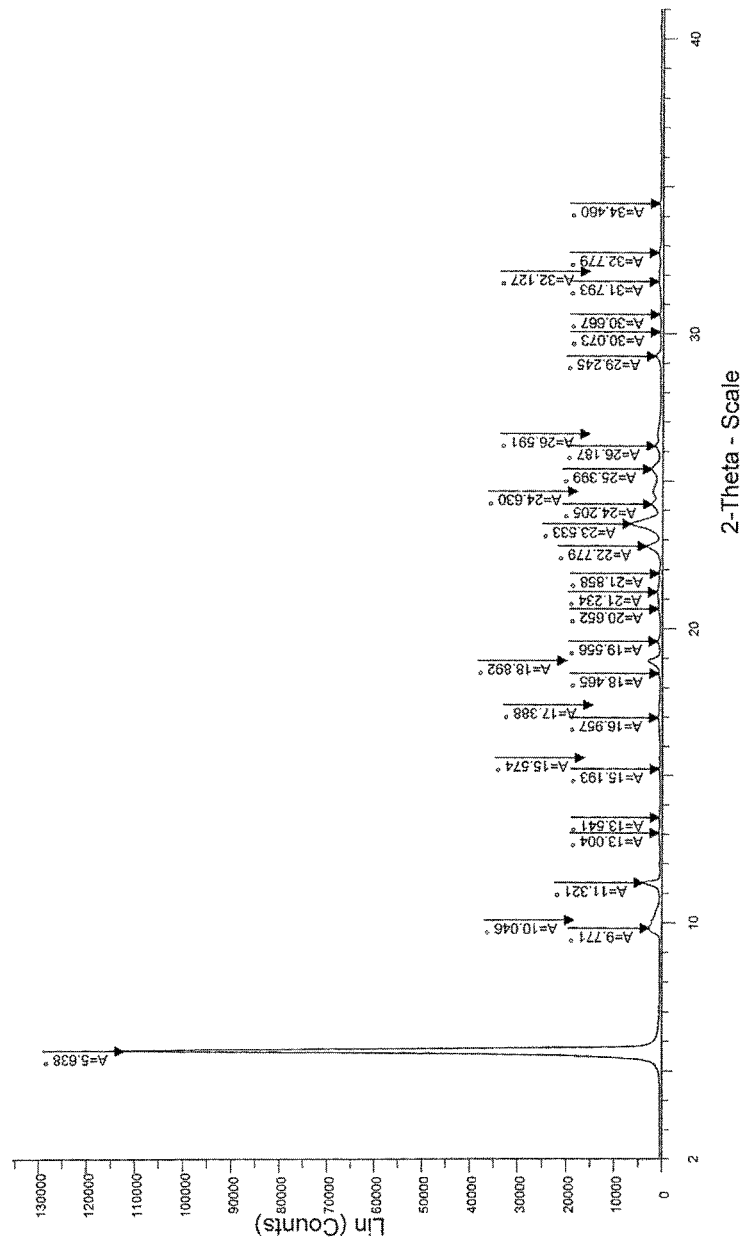
FIG. 1 is Illustration of X-ray powder diffraction (XRPD) pattern of Erlotinib hydrochloride-Form SE, prepared according to Example-3
Figure 2:
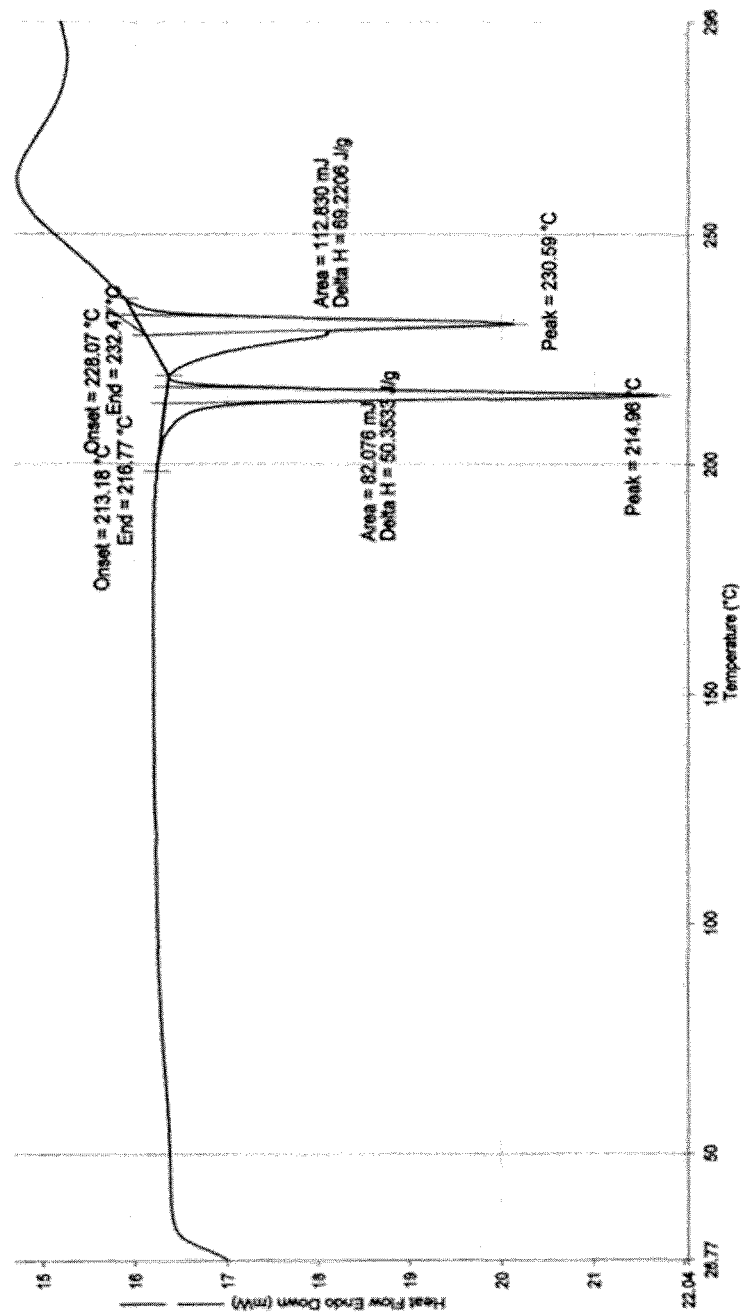
FIG. 2 is an Illustration of a differential scanning calorimetric ("DSC") curve of Erlotinib hydrochloride-Form SE, prepared according to Example-3
Figure 3:
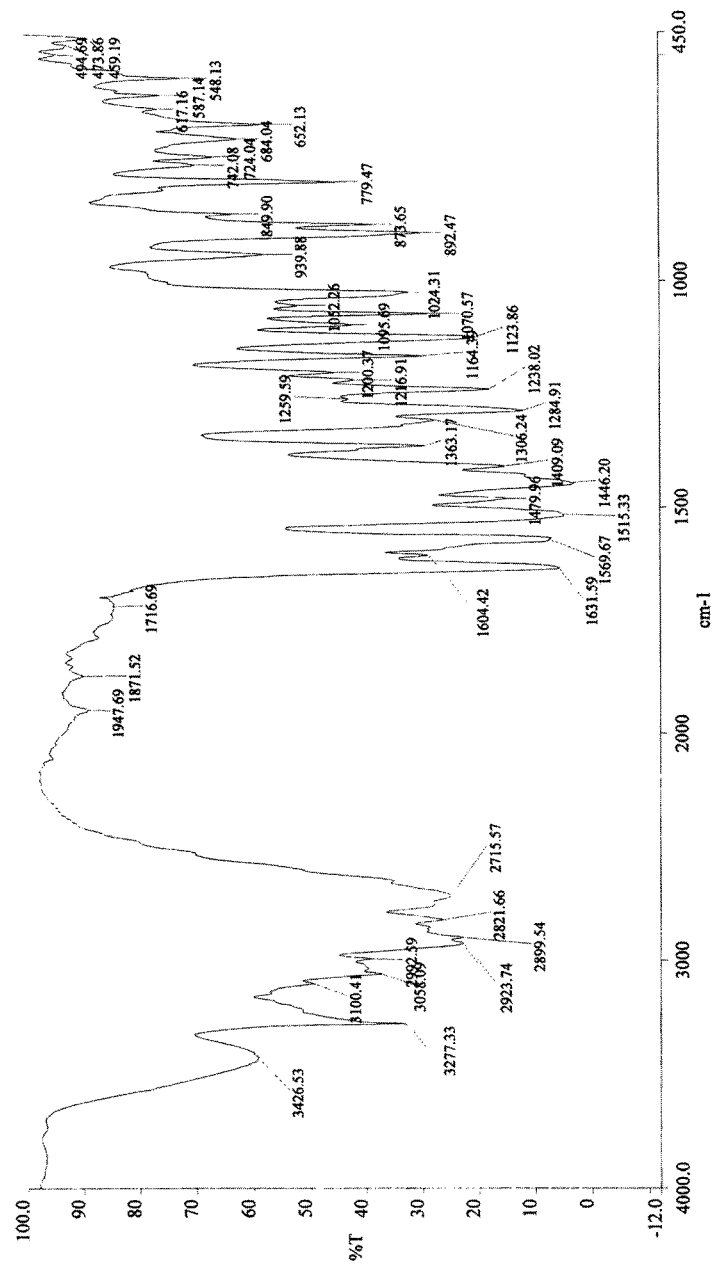
FIG. 3 is an Illustration of a IR spectrum of Erlotinib hydrochloride-Form SE, prepared according to Example-3

Erlotinib hydrochloride crystalline Form-SE of the present invention is further characterized by X-ray powder diffraction pattern substantially according to FIG. 1, DSC isothermal pattern substantially according to FIG. 2 and IR absorption spectrum substantially according to FIG. 3.

Minor variations in the observed 2 θ° angles values may be expected based on the analyst person, the specific XRPD diffractometer employed and the sample preparation technique. Further possible variations may also be expected for the relative peak intensities, which may be largely affected by the non-uniformity of the particle size of the sample. Hence, identification of the exact crystalline form of a compound should be based primarily on observed 2 theta angles with lesser importance attributed to relative peak intensities. The 2 theta diffraction angles and corresponding d-spacing values account for positions of various peaks in the X-ray powder diffraction pattern. D-spacing values are calculated with observed 2 theta angles and copper K a wavelength using the Bragg equation well known to those of having skill in the art of XRPD diffractometry science.

Figure 4:
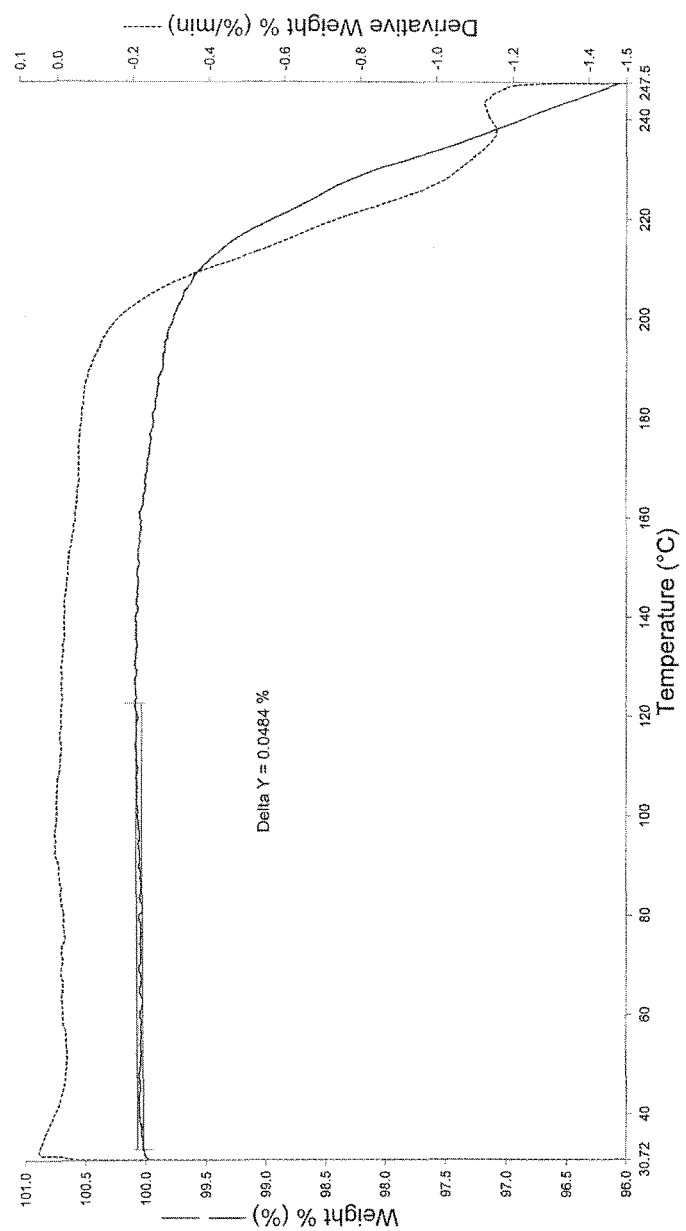
FIG. 4 is an Illustration of a TGA thermo gram of Erlotinib hydrochloride-Form SE, prepared according to Example-3

In view of possibility of marginal error in the assigning 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of Erlotinib hydrochloride over FIG. 1 and readily determine whether the X-ray diffraction pattern of the unidentified form is substantially the same as the X-ray powder diffraction pattern of the crystalline form of this invention. If the X-ray powder diffraction pattern is substantially the same as FIG. 1, the previously unknown crystalline form of Erlotinib hydrochloride can be readily and accurately identified as the crystalline Form SE of this invention. The crystalline Form-SE of Erlotinib hydrochloride is an anhydrate, which may be evident from the FIG. 4 showing the TGA thermogram. A sample of the crystalline Form SE prepared by the inventors had moisture content upto about 0.3% w/w by KF method, which also confirmed the anhydrate nature of the compound. While the invention is not limited to any specific theory, it should be understood however that the crystalline form SE of Erlotinib hydrochloride may contain additional residual or unbound moisture without losing its anhydrate character and/or its anhydrate crystalline form-SE characteristics. Nevertheless, one of the skill in the art should be able to determine whether they are same crystalline forms or not, by looking at the overall shape of the X-ray powder diffraction pattern optionally with help of other thermal data like DSC or TGA.

In yet another embodiment of the present invention, it provide a process/es for preparing Erlotinib hydrochloride crystalline Form-SE is characterized by X-ray powder diffraction pattern comprising at least 5 characteristic 2θ° peaks selected from the XRPD peak set of 5.60, 10.00, 11.40, 13.00, 13.50, 15.20, 18.40, 20.65, 21.86, 23.5, 31.80, 32.13, 32.80, 34.40±0.20 2θ°, DSC isotherm comprising the endothermic peaks ranging between 213 to 217° C. (Peak −1) and 225 to 235° C. (Peak −2) and IR absorption characteristic peaks at approximately 3278 cm$^{-1}$, 1948 cm$^{-1}$, 1871 cm$^{-1}$, 1632 cm$^{-1}$, 1164 cm$^{-1}$, 1024 cm$^{-1}$, 940 cm$^{-1}$ and 742 cm$^{-1}$ comprising the steps of—
  a. Combining the Erlotinib free base or salt with a mixture of ketone and alcohol solvent both having water content upto less than 0.5% w/w
  b. raise the temperature upto about 40-70° C.
  c. Stir the solution at same temperature up to a time between 15 to 60 minutes.
  d. combine isopropanol and HCl mixture
  e. optionally maintain the mixture for 10-60 minutes
  f. cooling the mixture upto about 10-40° C.
  g. isolating the crystalline material Step of combining the Erlotinib free base or salt with a mixture of ketone and alcohol comprise either mixing or suspending or making solution with Erlotinib free base or salt obtained by any process/any form with a readymade or freshly prepared mixture of ketone and alcohol solvent both having individually as well as after mixing—a water content up to less than 0.5% w/w.

In the process of preparing mixed solvent solution, alcohol solvent is selected from C2 to C4 alcohol and ketone solvent may be selected from C3 to C10 ketone. In one of the particular embodiment, C3 alcohol as isopropanol and C6 ketone as methyl isobutyl ketone (MIBK) was used for preparing Form-SE.

Preparation of mixed solvent solution of ketone and alcohol comprise a mixture of ketone and alcohol solvent having ratio between 30:70 to 70:30 v/v. In one of the particular embodiment, solvent mixture utilized for making Form SE was of alcohol and ketone in ratio of (50:50 v/v).

During combining Erlotinib free base or salt with a mixture of ketone and alcohol, a ratio of Erlotinib free base or salt w.r.t. mixture of ketone and alcohol is important in order to obtain the specifics of the crystalline polymorph to meet, which comprise a range between 1:30-70 (w/v). More preferably, this range may be 1:40-60 (w/v).

Any form of Crude or Pure Erlotinib base or its hydrochloride salt obtained by known processes may be used for preparing Form-SE.

In the step of raising the temperature in the range about 40-70° C., it preferred to raise the heating gradually followed by continued stir the solution at same temperature up to a time ranging between 15 to 60 minutes.

In steps of combining isopropanol and HCl mixture, it is comprising of slow addition of isopropanol (IPA) and HCl mixture, wherein isopropanol and HCl mixture prepared earlier by combining HCl gas and IPA is comprising of HCl strength ranging between 5 to 20% w/v.

After combining this acidic alcohol mixture, the solution may optionally be maintain under stirring for a time ranging between 10-60 minutes in order to retain the maximum hydro chlorination with unreacted erlotinib base present if any. If the process is started with Erlotinib HCl salt, this step may not be desired and the solution may be subjected to cooling simultaneously.

The step of cooling the mixture may be carried out for the mixture upto about 10-40° C. as per need to attain the crystalline material precipitated out with no or minimal possible degradation if any. Simultaneously, it is also essentially required to cool the solution in the successive lower rate of cooling in order to retain the characteristics of Form-SE, while achieving the pure crystal formation.

The process related impurities, including unreacted intermediates, side products, degradation products and other medium dependent impurities, that appears in the impurity profile of the Erlotinib hydrochloride can substantially be removed by the process of the present invention resulting in the formation crystalline form-SE. A substantially pure product having purities more than 99.5% (by HPLC) can be obtained by the process of the present invention. In view of maintaining the equilibrium to the impurity profile compliance, the process requires quality checks, while raising the temperature, wherever required upto 40-70° C.

The product may be isolated from the reaction mass by conventional processes including filtering and optional drying, which may be carried out at room temperature for the suitable durations to retain the crystalline polymorphic form characteristics.

Crystalline Form-SE can be recovered by conventional processes, which are not limited to scrapping, breaking, triturating and if required conventional drying.

Erlotinib hydrochloride crystalline Form-SE obtained according to present invention shall be dried under vacuum to attain water content in the range between 0.1 to 1.0% w/w In yet further another embodiment, it provides that the Crystalline Form SE of Erlotinib HCl obtained by the processes of the present application may be formulated as solid compositions for oral administration in the form of capsules, tablets, pills, powders or granules useful in the treatment of hyper-proliferative disorders, such as cancer.

Crystalline Form-SE of Erlotinib HCl of the present invention may have one or more advantageous and desirable properties compared to the known Erlotinib HCl, which are not limited to better stability, solubility and quality parameter leading to improved storage and distribution.

The Crystalline Form-SE of Erlotinib HCl described herein characterized by X-ray powder diffraction pattern (XRPD) and IR absorption spectra and Thermal techniques such as differential scanning calorimetric (DSC) Analysis, TGA. The samples of Erlotinib HCl Crystalline Form-SE were analyzed by XRPD on a Bruker AXS D8 Advance Diffractometer using X-ray source—Cu K$\alpha$ radiation using the wavelength 1.5418 Å, however, DSC analysis were carried out on a Perkin Elmer Jade instrument and TGA analysis were carried out on Perkin Elmer Pyris 1.0 instrument. Illustrative examples of analytical data for the Crystalline Form-SE of Erlotinib HCl obtained in the Examples are set forth in the FIGS. 1-4.

In another embodiment, the Erlotinib HCl Crystalline Form-SE obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerin, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Form-SE of Erlotinib HCl of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Crystalline Form-SE of Erlotinib HCl of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXPERIMENTAL DETAILS

The process for preparation according to the present invention of crystalline Erlotinib HCl Form-SE may be demonstrated by examples as given below.

Example 1

Preparation of Erlotinib Hydrochloride Form-SE from Erlotinib Free Base

Charge mixture of 1.5 lit MIBK:IPA (50:50) in a clean three necked round bottom flask and stir for about 10 minutes. Add 30.0 gm Erlotinib (free base) at room temperature under stirring. Raise the temperature of reaction mixture up to 60-65° C. and stir for about 30 min. and ensure the solution to become clear. Filter this solution through membrane filter.

Collected clear filtrate taken into clean three necked round bottom flask and temperature is raised to again at 60-65° C. under stirring to maintain the clear solution. Start adding slowly added IPA:HCl solution (about 14% v/w) at 60-65° C. under stirring.

Cool the reaction solution to room temperature naturally and stir for about 30 minutes at room temperature.

Filter the separated solid and subject it to drying at about 60-70° C. under vacuum for nearly 12 hrs.

Yield: 30.0 g

H. Individual Impurity=0.04%; Total impurities=0.2%; Water content=0.2%

Purity: 99.8% (By HPLC purity)

Example 2

Preparation of Crystalline Erlotinib Hydrochloride (Form-SE)

Take about 30.0 gm Erlotinib (free base) in a clean three necked round bottom flask. Add about 1500 ml mixture of MIBK:IPA (1:1 ratio) at room temperature under stirring and maintain the stirring for about 10-15 minutes. Raise the temperature of reaction mixture up to 60-65° C. and stir for about 30 min. to attain the clear solution. Filter this solution through membrane filter and the clear filtrate is taken into clean three necked round bottom flask. Temperature is raised to again at 60-65° C. under stirring to maintain the clear solution. Start adding slowly added IPA:HCl solution (about 13-15% v/w) at 60-65° C. under stirring. Maintain the solution for 30 minutes and later on cool the reaction solution to room temperature naturally and stir for about 30 minutes at room temperature. Filter the separated solid and subject it to drying at about 60-70° C. under vacuum for nearly 12 hrs.

Dry weight=29.6 g

H. Individual Impurity=0.04%; Total impurities=0.18%; Water content=0.3%

XRPD as per FIG. 1; and DSC as per FIG. 2

Example 3

Preparation of Crystalline Erlotinib Hydrochloride (Form-SE)

Charge 1500 ml mixture of MIBK:IPA (1:1 ratio; Moisture Content 0.25%) in a clean three necked round bottom flask and stir for about 10 minutes. Add 30.0 gm Erlotinib (free base) at room temperature under stirring and maintain the stirring for about 10-15 minutes. Heat the reaction mixture up to 60-65° C. and stir for about 30 min. to get the clear solution. Filter the solution and the filtrate is taken into clean flask. Temperature is again raised to about 60-65° C. under stirring to retain the clarity of solution. Now add slowly IPA:HCl solution (about 13-15% v/w) at 60-65° C. under stirring. Maintain the solution for 10-20 minutes and later on cool the reaction solution to room temperature. Stir the solution for about 30 minutes at room temperature. Filter the isolated crystalline material. Dry the material at about 60-70° C. under vacuum for 10-12 hrs.

Yield: 29.2 g

H. Individual Impurity=0.04%; Total impurities=0.19% w/w

Chromatographic purity (By HPLC) ~99.81%

Water Content (By KF) ~0.3% w/w

DSC Melting Peak (1)=214.96° C.

Peak (2)=230.59° C.

IR absorption peaks at approximately 3278 $cm^{-1}$, 1948 $cm^{-1}$, 1871 $cm^{-1}$, 1632 $cm^{-1}$, 1164 $cm^{-1}$, 1024 $cm^{-1}$, 940 $cm^{-1}$ and 742 $cm^{-1}$.

Example 4

Large Scale Preparation of Crystalline Erlotinib Hydrochloride-Form-SE

1. Charge 50 L premix mixture of MIBK:IPA (ratio about 1:1 v/v; Moisture Content=0.2% w/w) in a GLR flask and stir for about 10-15 min.
2. Add Erlotinib (as free base) (~1 kg) at room temperature under continued stirring
3. Heat the reaction mixture up to 60-65° C. and stir for about 30 min (Solution should be clear).
4. Filter the hot solution through membrane filter.
5. Collect the clear filtrate and again charge into a clean GLR flask
6. Heated the solution again up to about 60-65° C. under stirring to maintain the clear solution
7. Slowly add 1.33 lit IPA:HCl solution (prepared strength about 13-15% v/w) in one hour at 60-65° C. under stirring through addition tank.
8. Cool the reaction mass to room temperature
9. Stir for about 30 min at room temperature.
10. Filter the separated crystalline material.
11. Collect crystalline material and dry at 60-70° C. under vacuum for about 10-12 hrs.

Yield: 1002 gm (dry weight)

H. Individual Impurity=0.04%; Total impurities=0.16% w/w; Water content=0.20%

The abovementioned examples, which are provided by way of illustration, should not be construed as limiting the scope of the invention with respect to parameter/s, ingredient/s and quantities used in any manner.

We claim:

1. Erlotinib hydrochloride (I) crystalline Form-SE characterized by X-ray powder

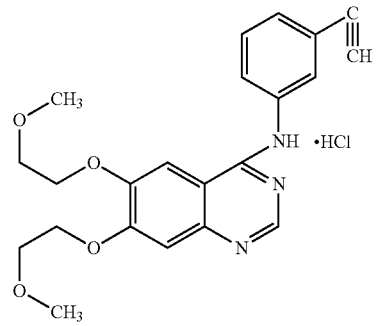

diffraction pattern according to FIG.-1.

* * * * *